United States Patent
Ray, II et al.

(10) Patent No.: US 10,660,962 B2
(45) Date of Patent: *May 26, 2020

(54) SILICONE-BASED COMPOSITION FOR SKIN TREATMENT

(71) Applicant: CMPD Licensing, LLC, Conroe, TX (US)

(72) Inventors: Jay Richard Ray, II, Conroe, TX (US); Charles D. Hodge, Conroe, TX (US)

(73) Assignee: CMPD Licensing, LLC, Conroe, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/121,184

(22) Filed: Sep. 4, 2018

(65) Prior Publication Data

US 2019/0060464 A1 Feb. 28, 2019

Related U.S. Application Data

(63) Continuation of application No. 15/457,003, filed on Mar. 13, 2017, now Pat. No. 10,064,949, which is a continuation of application No. 13/564,467, filed on Aug. 1, 2012, now Pat. No. 9,592,241, which is a continuation of application No. 13/337,614, filed on Dec. 27, 2011, now abandoned.

(51) Int. Cl.

| | |
|---|---|
| *A61K 47/34* | (2017.01) |
| *A61K 9/00* | (2006.01) |
| *A61K 47/24* | (2006.01) |
| *A61K 9/06* | (2006.01) |
| *A61K 31/67* | (2006.01) |
| *A61K 31/195* | (2006.01) |
| *A61K 31/4545* | (2006.01) |
| *A61K 31/695* | (2006.01) |
| *A61K 31/56* | (2006.01) |
| *A61K 45/06* | (2006.01) |
| *A61K 47/22* | (2006.01) |
| *A61K 47/10* | (2017.01) |
| *A61K 31/167* | (2006.01) |

(52) U.S. Cl.
CPC ............. *A61K 47/34* (2013.01); *A61K 9/0014* (2013.01); *A61K 9/06* (2013.01); *A61K 31/167* (2013.01); *A61K 31/195* (2013.01); *A61K 31/4545* (2013.01); *A61K 31/56* (2013.01); *A61K 31/695* (2013.01); *A61K 45/06* (2013.01); *A61K 47/10* (2013.01); *A61K 47/22* (2013.01); *A61K 47/24* (2013.01)

(58) Field of Classification Search
CPC .............. A61K 31/4545; A61K 31/195; A61K 31/167; A61K 31/56; A61K 31/695; A61K 9/06; A61K 9/0014; A61K 47/10; A61K 47/22; A61K 47/24; A61K 47/34; A61K 45/06

See application file for complete search history.

(56) References Cited

U.S. PATENT DOCUMENTS

| | | | | |
|---|---|---|---|---|
| 2006/0013866 | A1* | 1/2006 | Carter | .................. A61K 9/0009 |
| | | | | 424/449 |
| 2008/0153786 | A1* | 6/2008 | Andres | ................ A61K 9/0014 |
| | | | | 514/167 |

FOREIGN PATENT DOCUMENTS

WO WO-2011022652 A1 * 2/2011 ......... A61K 2300/00

* cited by examiner

*Primary Examiner* — Sarah Pihonak
(74) *Attorney, Agent, or Firm* — Akerman LLP

(57) ABSTRACT

The present embodiments may relate to topically delivered compounded medications for the treatment of scar tissue, skin disorders, and/or other ailments. In one aspect, a transdermal cream or gel may provide for the effective administration of multiple medications simultaneously. Preferably, a silicone-based gel may be provided as a base composition and may have a non-zero percentage of silicone or silicone variant. The silicone-based gel may comprise cyclopentasiloxane, polysilicone-11, dimethicone, and C30-45 alkyl cetearyl dimethicone crosspolymer, and include several active ingredients, such as glucocorticoids, antihistamines, and nerve depressants. The silicone-based gel may include a combination of fluticasone, loratadine, and gabapentin. The concentrations of fluticasone and loratadine may be relatively low, while that of gabapentin moderately high. The silicone-based gel may also have one or more local anesthetics, such as prilocaine and/or lidocaine. The silicone-based gel may include additional active ingredients, such as NSAIDs, anticonvulsants, antidepressants, muscle relaxants, and/or other active ingredients.

14 Claims, 1 Drawing Sheet

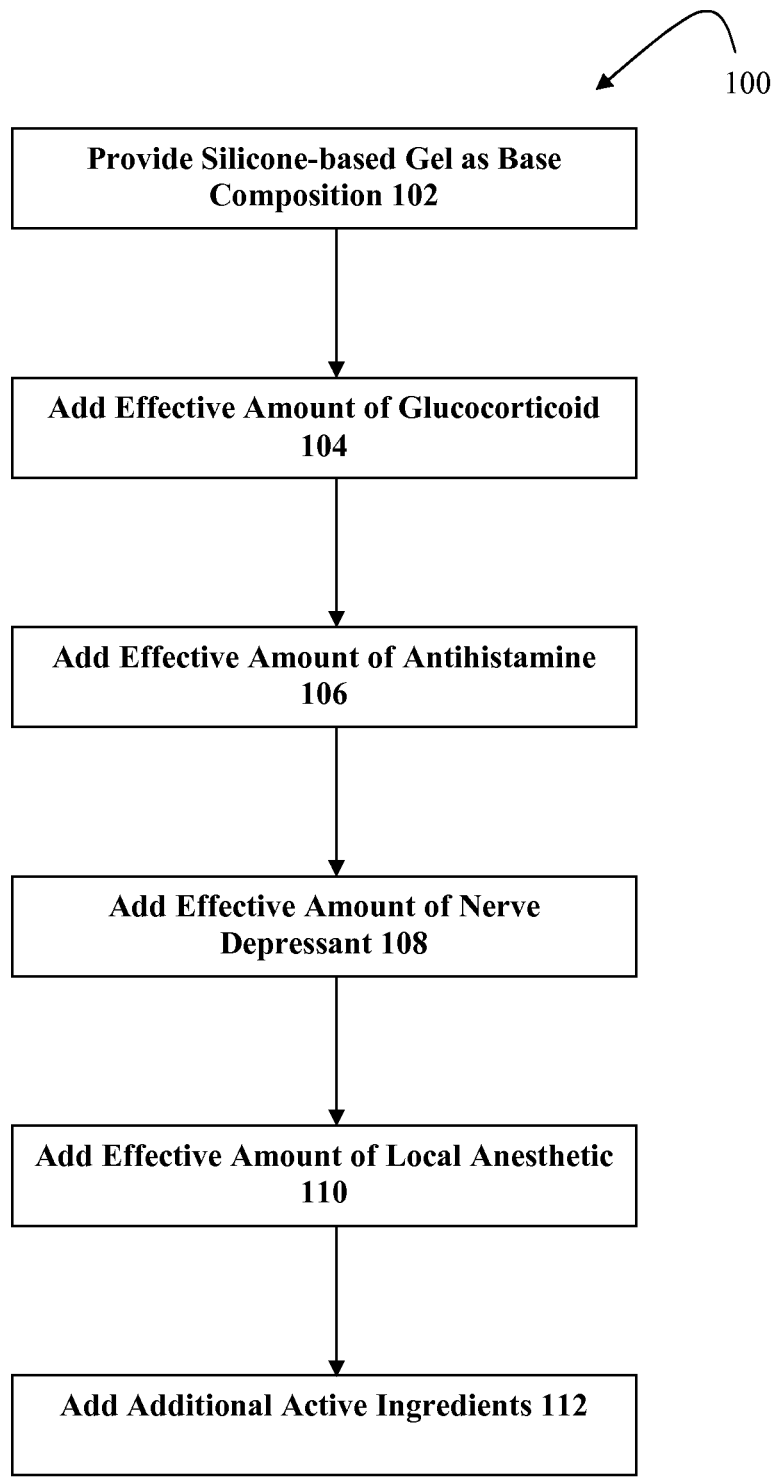

SILICONE-BASED COMPOSITION FOR SKIN TREATMENT

CROSS-REFERENCE TO RELATED APPLICATIONS

This patent application is a continuation of U.S. patent application Ser. No. 15/457,003, entitled Silicone-Based Composition for Skin Treatment, filed Mar. 13, 2017, which is a continuation of U.S. patent application Ser. No. 13/564,467, entitled Silicone-Based Composition for Skin Treatment, filed Aug. 1, 2012, now U.S. Pat. No. 9,592,241, which is a continuation of U.S. patent application Ser. No. 13/337,614, entitled Silicone-Based Composition for Skin Treatment, filed on Dec. 27, 2011, now abandoned, the contents of which are incorporated by reference herein in their entirety.

FIELD OF THE INVENTION

The present application relates to skin treatment. In particular, the present application relates to transdermal creams or gels for topically applying several medications to treat skin disorders and/or scar tissue.

BACKGROUND

Traditional compositions used for the treatment of scars may include silicone. For example, conventional compositions include those disclosed by U.S. Pat. No. 6,827,929 (entitled "Scar Treatment Composition"); U.S. Pat. No. 6,337,076 (entitled "Method and Composition for the Treatment of Scars"); U.S. Publication No. 2011/0046532 (entitled "Composition Including a Silicone-based Polymer and a Method of Treating Skin Disorders Using the Composition"); U.S. Publication No. 2010/0322875 (entitled "Silicone Scar Treatment Preparation"); U.S. Publication No. 2009/0143333 (entitled "Silicone Gel-based Compositions for Wound Healing and Scar Reduction"); and U.S. Publication No. 2006/0029672 (entitled "Silicone Gel Composition and Dispenser Therefor"), which are all incorporated herein by reference in their entireties. However, conventional compositions may include various drawbacks, such as addressing limited medical conditions; having inadequate or ineffective active ingredients; exhibiting poor permeation, pain relief, healing qualities, storage characteristics, and/or other drawbacks.

SUMMARY

The present embodiments may relate to topically delivered compounded medications for the treatment of scar tissue, skin disorders, and/or other ailments. In one aspect, a transdermal cream or gel that is silicone-based may provide for the effective administration of multiple medications simultaneously. The silicone-based gel may include several active ingredients, such as a glucocorticoid, an antihistamine, a nerve depressant, and one or more local anesthetics. The silicone-based gel may include additional active ingredients as well, such as NSAIDs (Non-Steroidal Anti-Inflammatory Drugs), anticonvulsants, antidepressants, muscle relaxants, and/or other active ingredients. The present embodiments also may relate to methods of manufacturing silicone-based transdermal creams or gels.

In one aspect, a silicone-based gel for topical application and the treatment of scar tissue may be provided. The silicone-based gel may include a non-zero percentage of silicone or a silicone variant, and a first active ingredient in a first amount of between approximately 0.1% and approximately 5.0% by weight of the silicone-based gel. The first active ingredient may be a glucocorticoid. The silicone-based gel may include a second active ingredient in a second amount of between approximately 0.1% and approximately 5.0% by weight of the silicone-based gel. The second active ingredient may be an antihistamine. As a result, the topical application of the silicone-based gel may allow for the transdermal administration of the first and second active ingredients simultaneously.

In another aspect, a silicone-based gel for topical application and the treatment of scar tissue may be provided. The silicone-based gel may include a non-zero percentage of silicone or a silicone variant, and a first active ingredient in a first amount of between approximately 0.1% and approximately 5.0% by weight of the silicone-based gel. The first active ingredient may be fluticasone. The silicone-based gel may include a second active ingredient in a second amount of between approximately 0.1% and approximately 5.0% by weight of the silicone-based gel. The second active ingredient may be loratadine. As a result, the topical application of the silicone-based gel may allow for the transdermal administration of the first and second active ingredients simultaneously.

In another aspect, a silicone-based gel for topical application and treatment of scar tissue may be provided. The silicone-based gel may include a non-zero percentage of silicone or a silicone variant, and a first active ingredient in a first amount of between approximately 0.1% and approximately 5.0% by weight of the silicone-based gel. The first active ingredient may be a glucocorticoid, such as fluticasone. The silicone-based gel may include a second active ingredient in a second amount of between approximately 0.1% and approximately 5.0% by weight of the silicone-based gel. The second active ingredient may be an antihistamine, such as loratadine. The silicone-based gel may include a third active ingredient in a third amount of between approximately 5.0% and approximately 25.0% by weight of the silicone-based gel. The third active ingredient may be a nerve depressant, such as gabapentin. The silicone-based gel may include at least one local anesthetic, such as lidocaine and/or prilocaine, in an amount of between approximately 1.0% and approximately 7.0% by weight of the silicone-based gel. As a result, the topical application of the silicone-based gel may allow for the transdermal administration of the first, second, and third active ingredients simultaneously.

In another aspect, a silicone-based gel for topical application and treatment of scar tissue may be provided. The silicone-based gel may include cyclopentasiloxane; polysilicone-11; dimethicone; and C30-45 alkyl cetearyl dimethicone crosspolymer. The silicone-based gel may include one or more active ingredients. The one or more active ingredients may comprise a glucocorticoid and/or an antihistamine such that the silicone-based gel facilitates the treatment of scar tissue. The silicone-based gel may include both a glucocorticoid and an antihistamine, both in an amount of between approximately 0.1% and approximately 5.0% by weight of the silicone-based gel, with the glucocorticoid comprising fluticasone and the antihistamine comprising loratadine. The silicone-based gel may also include a third active ingredient in an amount of between approximately 5.0% and approximately 25.0% by weight of the silicone-based gel, and at least one local anesthetic. The third active ingredient may be a nerve depressant, such as gabapentin.

The above-described and other features and advantages of the present disclosure will be appreciated and understood by those skilled in the art from the following detailed description, drawings, and appended claims.

BRIEF DESCRIPTION OF THE DRAWINGS

There is shown in the drawing embodiments which are presently preferred, it being understood, however, that the invention can be embodied in other forms without departing from the spirit or essential attributes thereof.

FIG. 1 depicts an exemplary method of making a silicone-based composition for treating scars and/or skin disorders.

DETAILED DESCRIPTION OF THE INVENTION

The present embodiments relate to topically delivered compounded medications for the treatment of scar tissue, skin disorders, and/or other ailments. In one aspect, a transdermal cream or gel that is silicone-based may provide for the effective administration of multiple medications simultaneously. The silicone-based gel may include several active ingredients, such as a glucocorticoid, an antihistamine, a nerve depressant, and one or more local anesthetics. The silicone-based gel may include additional active ingredients as well, such as NSAIDs, anticonvulsants, antidepressants, muscle relaxants, and/or other active ingredients.

The silicone-based gel may be used for topical application of compounded therapies. In one embodiment, the silicone-based gel may be approximately 85.0% or more silicon, and up to approximately 15.0% active ingredients. Other percentages may be used. The silicone-based gel may include a relatively high level of "stickiness," such as more stickiness than that which exists with conventional gels. The silicone-based gel may be used for scar treatments and/or a wide variety of other disease states and needs.

The silicone-based gel may include several ingredients. In one aspect, the silicone-based gel may include cyclopentasiloxane, polysilicone-11, dimethicone, and/or C30-45 alkyl cetearyl dimethicone crosspolymer. The silicone-based gel may also include tocopheryl acetate, BHT (butylated hydroxytoluene), Lipoderm® core technology or bases available from PCCA, and/or other ingredients.

In one aspect, a silicone-based gel for topical application and the treatment of scar tissue may be provided. The silicone-based gel may include a non-zero percentage of silicone or a silicone variant, such as at least approximately 50%, 75%, or more of the silicone-based gel; and a first active ingredient in a first amount of between approximately 0.1% and approximately 5.0% by weight of the silicone-based gel. The first active ingredient may be a glucocorticoid, such as fluticasone. The silicone-based gel may include a second active ingredient in a second amount of between approximately 0.1% and approximately 5.0% by weight of the silicone-based gel. The second active ingredient may be an antihistamine, such as loratadine. As a result, the topical application of the silicone-based gel may allow for the transdermal administration of the first and second active ingredients simultaneously.

The silicone-based gel may further comprise a third active ingredient in a third amount of between approximately 5.0% and approximately 25.0% by weight of the silicone-based gel. The third active ingredient may comprise a nerve depressant, such as gabapentin. The silicone-base gel may further comprise lidocaine and/or prilocaine. The amount of lidocaine and/or prilocaine may each be between approximately 1.0% and approximately 7.0% by weight of the silicone-based gel. The silicone-based gel may comprise a fourth active ingredient in a fourth amount of between approximately 0.05% and approximately 15.0% by weight of the silicone-based gel. The fourth active ingredient may include a NSAID, a muscle relaxant, an anticonvulsant, an antidepressant, and/or other active ingredients.

In another aspect, a silicone-based gel for topical application and treatment of scar tissue may be provided. The silicone-based gel may include a non-zero percentage of silicone or a silicone variant, such as at least approximately 50%, 75%, or more of the silicone-based gel; and a first active ingredient in a first amount of between approximately 0.1% and approximately 5.0% by weight of the silicone-based gel. The first active ingredient may be a glucocorticoid, such as fluticasone. The silicone-based gel may include a second active ingredient in a second amount of between approximately 0.1% and approximately 5.0% by weight of the silicone-based gel. The second active ingredient may be an antihistamine, such as loratadine. The silicone-based gel may include a third active ingredient in a third amount of between approximately 5.0% and approximately 25.0% by weight of the silicone-based gel. The third active ingredient may be a nerve depressant, such as gabapentin. The silicone-based gel may include at least one local anesthetic, such as lidocaine and/or prilocaine, in an amount between approximately 1.0% and approximately 7.0% by weight of the silicone-based gel. As a result, the topical application of the silicone-based gel may allow for the transdermal administration of the first, second, and third active ingredients simultaneously, and may provide medications that facilitate healing and relief from itching, skin irritation, pain and/or other discomfort at the same time.

In another aspect, a silicone-based gel for topical application and treatment of scar tissue may be provided. The silicone-based gel may include cyclopentasiloxane; polysilicone-11; dimethicone; and/or C30-45 alkyl cetearyl dimethicone crosspolymer. The silicone-based gel may include one or more active ingredients. The one or more active ingredients may comprise a glucocorticoid and/or an antihistamine. The silicone-based gel may include both a glucocorticoid and an antihistamine, both in an amount of between approximately 0.1% and approximately 5.0% by weight of the silicone-based gel, with the glucocorticoid comprising fluticasone and the antihistamine comprising loratadine. The silicone-based gel may also include a nerve depressant, such as gabapentin, in an amount of between approximately 5.0% and approximately 25.0% by weight of the silicone-based gel, and one or more local anesthetics, such as lidocaine and prilocaine.

I. Exemplary Silicone-Based Gel

The transdermal cream or gel may be silicone-based and include several medications for topical application. Preferably, the base composition of the transdermal cream or gel may be a silicone-based gel. The silicone-based gel may have a non-zero percentage of silicone and/or any variation thereof. The silicone-based gel may include at least approximately 10%, 25%, 50%, 60%, 70%, 80%, 90% or more, or other percentages of silicone and/or any variations of silicone.

For instance, the silicone-based gel may include at least approximately 50%, approximately 75%, or more silicone and/or silicone variant, with the remainder of the silicone-based gel comprising active and/or other ingredients. In one embodiment, the transdermal cream or gel uses a silicone-based gel as a base and includes several active ingredients that are added to the silicon-based gel. The final transdermal cream or gel using the silicone-based gel as a base may include at least approximately 50%, 75%, or 90% or more silicone or silicone variant, with the remaining percentage of the final transdermal cream or gel comprising active or other ingredients.

The silicone may facilitate the permeation of one or more medications in the silicone-based gel through the skin of a patient when the silicone-based gel is topically applied. The silicone may be a polymer, such as plastic or rubber, that contains silicon. Silicone variants or variations of silicone that may be used with the silicone-based gel may include silicone or silicone derivatives that are in gel, fluid, powder, or other forms. The silicone or silicone variants may include silicon, silicon oxide, silicon dioxide, silica, medical grade silicone, professional grade silicone, or other forms of silicone and/or silicon.

The silicone-based gel may be used to treat scar tissue, burns, wrinkles, skin lines, brown spots, acne scars, stretch marks, dark spots, warts, moles, and/or other skin disorders. For instance, the silicone-based gel may reduce or lighten scars, such as scars resulting from surgery or burns. The silicone-based gel may relieve itching and/or discoloration, such as redness to make scars or marks less noticeable. The silicone and silicone variants may be applied in the form of a silicone gel sheet, a self-adherent silicone dressing, a cream or gel topically applied from a tube, a patch, and/or other delivery means.

The silicone-based gel may be topically applied in various regimes. For instance, the silicone-based gel may be applied once or twice daily for a number of days. The silicone-based gel may be applied for several hours at a time and over a substantial period of time, such as eight to twelve weeks. The silicone-based gel may exhibit excellent storage characteristics, and avoid separation and/or degradation of the active ingredients from the base for substantial lengths of time.

In one embodiment, a silicone-based gel for topical application and treatment of scar tissue may be provided. The silicone-based gel may include Lipoderm® core technology and ingredients, and/or include cyclopentasiloxane; polysilicone-11; dimethicone; and/or C30-45 alkyl cetearyl dimethicone crosspolymer. Briefly, cyclopentasiloxane is a type of silicone, and may have the ability to lubricate, and may be waterproof and provide shine. Cyclopentasiloxane may have a very sticky consistency, and may be volatile and/or used in combination with dimethicone. The cyclopentasiloxane may be combined with polysilicone-11, which may be a synthetic crosslinked siloxane that functions as a film-forming agent and polymer, and/or C30-45 alkyl cetearyl dimethicone crosspolymer, which may be a copolymer of C30-45 alkyl cetearyl dimthicone crosslinked with vinyl cyclohexene oxide, or another copolymer. The silicone-based gel may include additional, fewer, or alternative ingredients, including one or more active ingredients.

In another embodiment, the silicone-based gel may be a conventional composition, such as those disclosed by U.S. Pat. Nos. 6,827,929; 6,337,076; U.S. Publication No. 2011/0046532; U.S. Publication No. 2010/0322875; U.S. Publication No. 2009/0143333; and/or U.S. Publication No. 2006/0029672, which are all incorporated herein by reference in their entireties. Silicone-based gels having additional, fewer, or alternate ingredients may be used.

II. Exemplary Active Ingredients

The silicone-based cream or gel may include various combinations of medication. In one aspect, the silicone-based gel may include both a glucocorticoid and an antihistamine for simultaneous topical delivery. The silicone-based gel may include a relatively low concentration of both the glucocorticoid and the antihistamine, such as between approximately 0.1% and approximately 5.0% by weight.

Glucocorticoids may be anti-inflammatories that may be typically used in nasal sprays for rhinitis or inhalers for asthma. However, when used with a silicone-based gel of the present embodiments that is topically applied, a glucocorticoid may exhibit scar or wound healing properties or other beneficial effects.

A histamine antagonist or antihistamine is a drug that may inhibit action of histamine by preventing it from attaching to histamine receptors. When used with a silicone-based gel of the present embodiments that is topically applied, an antihistamine may relieve itching, such as itching associated with burns or scarred skin tissue. In other words, the combination of a glucocorticoid with an antihistamine in a silicone-based gel may alleviate itching while simultaneously healing the affected area and reducing the visual effects or unsightliness of any scarring or other skin disorder.

In another aspect, the silicone-based gel may include a glucocorticoid, an antihistamine, and a nerve depressant for simultaneous topical delivery. The silicone-based gel may include a relatively low concentration of both the glucocorticoid and the antihistamine (such as approximately 5.0% or less by weight), with a moderate-to-high concentration of the nerve depressant (such as between approximately 5.0% to approximately 25% by weight). The nerve depressant may be used to treat nerve pain in the affected area.

The silicone-based gel may also include two or more local anesthetics, such as lidocaine and prilocaine. A local anesthetic may be used to induce an absence of pain sensation in the affected area at which the silicone-based gel is topically applied. The silicone-based gel may include approximately equal concentrations of both lidocaine and prilocaine.

The silicone-based gel may include additional or alternative active ingredients. For instance, with patients experiencing chronic pain, such as with severe burns and scarring, the silicone-based gel may include NSAIDs, anticonvulsants, pain relievers, and/or other ingredients.

III. Exemplary Silicone-Based Gels for Compounded Therapy

In one aspect, a silicone-based gel may include a glucocorticoid, such as fluticasone, in an amount between approximately 0.1% and approximately 10.0% by weight of the silicone-based gel; an antihistamine, such as loratadine, in an amount between approximately 0.1% and approximately 10.0% by weight of the silicone-based gel; a nerve depressant, such as gabapentin, in an amount between approximately 5.0% and approximately 25.0% by weight of the silicone-based gel; a first local anesthetic, such as lidocaine, in an amount between approximately 0.5% and approximately 7.0% by weight of the transdermal cream; and a second local anesthetic, such as prilocaine, in an amount between approximately 0.5% and approximately 7.0% by weight of the transdermal cream. As a result, the silicone-based gel may allow for the topical administration of fluticasone, loratadine, gabapentin, lidocaine, and/or prilocaine simultaneously during use.

In one embodiment, the silicone-based gel may include fluticasone in an amount between approximately 0.1% and approximately 2.0% by weight of the silicone-based gel; loratadine in an amount between approximately 1.0% and approximately 3.0% by weight of the silicone-based gel; gabapentin in an amount between approximately 10.0% and approximately 20.0% by weight of the silicone-based gel; and lidocaine and prilocaine each in an amount between approximately 2.0% and approximately 4.0% by weight of the transdermal cream. In another embodiment, the silicone-based gel may comprise approximately 1.0% by weight fluticasone; approximately 2.0% by weight loratadine; approximately 15.0% by weight gabapentin; and approximately 3.0% by weight of both lidocaine and prilocaine.

IV. Exemplary Method of Compounding

FIG. 1 depicts an exemplary method of making a transdermal cream or gel with several active ingredients 100. The method 100 may include providing a silicone-based gel as a base composition 102; adding to the base composition: a glucocorticoid 104; an antihistamine 106; a nerve depressant 108; a local anesthetic 110; and/or other active ingredients 112. The method may include additional, fewer, or alternate steps.

The method 100 may comprise providing a base composition 102. The base composition may be a silicone-based gel. The silicone-based gel may include silicone and/or any variations thereof, including silicon and other variations discussed elsewhere herein. The amount of silicone or variant thereof in the final silicone-based gel may be at least approximately 50%, approximately 75%, or more of final silicone-based gel, with the remainder of the silicone-based gel comprising active and/or other ingredients. Other amounts of silicone may be used, including those disclosed herein.

In one embodiment, the silicone-based gel may be primarily silicone and/or silicon based, with the remainder substantially comprising active and/or other ingredients. The silicone-based gel may include cyclopentasiloxane; polysilicone-11; dimethicone; and/or C30-45 alkyl cetearyl dimethicone crosspolymer. The silicone-based gel may also include tocopheryl acetate, BHT (butylated hydroxytoluene), a Lipoderm® base available from PCCA, and/or other ingredients. The silicone-based gel may include between approximately 0.1% and approximately 25.0% by weight cyclopentasiloxane; polysilicone-11; dimethicone; and/or C30-45 alkyl cetearyl dimethicone crosspolymer, respectively. Other percentages may be used.

The method 100 may include adding to the silicone-based gel or base composition a glucocorticoid 104. The glucocorticoid may be flutacasone or another glucocorticoid, such as dexamethasone, beclometasone, methylprednisolone, betamethasone, prednisone, cortisol, and other ingredients providing glucocorticoid effects. The glucocorticoid may be added in an amount such that the silicone-based gel includes a low concentration of glucocorticoid. The glucocorticoid may facilitate skin healing when the silicone-based gel is topically applied.

The glucocorticoid may comprise between approximately 0.1% and approximately 7.0% by weight of the silicone-based gel, preferably between approximately 0.1% and approximately 2.0%. Other amounts may be used, including those discussed elsewhere herein.

The method 100 may include adding to the silicone-based gel or base composition an antihistamine 106. The antihistamine may be loratadine or another Hi-receptor antagonist, such as azelastine, cetirizine, cyclizine, chlorpheniramine, clemastine, desloratadine, dexchlorpheniramine, dimenhydrinate, dimetindene, diphenhydramine, doxylamine, ebastine, embramine, fexofendaine, levocetirizine, meclozine, olopatadine, pheniramine, promethazine, quetiapine, rupatadine, cimetidine, famotidine, lafutidine, nizatidine, ranitidine, roxatidine, and/or other antihistamines. The antihistamine may be added in an amount such that the silicone-based gel includes a low concentration of antihistamine. The antihistamine may alleviate itching or irritation when the silicone-based gel is topically applied.

The antihistamine may comprise between approximately 0.1% and approximately 7.0% by weight of the silicone-based gel, preferably between approximately 2.0% and approximately 4.0%. Other amounts may be used, including those discussed elsewhere herein.

The method 100 may include adding to the silicone-based gel or base composition a nerve depressant 108. The nerve depressant may be gabapentin or another nerve depressant. The nerve depressant may be added in an amount such that the silicone-based gel includes a moderate to high concentration of antihistamine. The nerve depressant may alleviate pain when the silicone-based gel is topically applied.

The nerve depressant may comprise between approximately 1.0% and approximately 25.0% by weight of the silicone-based gel, preferably between approximately 10.0% and approximately 20.0%. Other amounts may be used, including those discussed elsewhere herein.

The method 100 may include adding to the silicone-based gel or base composition one or more local anesthetics 110. The one or more local anesthetics may include lidocaine and/or prilocaine, or other local anesthetics. The local anesthetic may alleviate pain when the silicone-based gel is topically applied.

The local anesthetics may be added in an amount such that the silicone-based gel includes a low to moderate concentration of anesthetic. For example, the local anesthetics may comprise between approximately 0.1% and approximately 7.0% by weight of the silicone-based gel, preferably between approximately 2.0% and approximately 4.0%. Other amounts may be used, including those discussed elsewhere herein.

The method 100 may include adding to the silicone-based gel or base composition additional active ingredients 112. The additional active ingredients may include NSAIDs, anticonvulsants, muscle relaxants, NMDA receptor antagonists, opiate or opioid agonists, antidepressants, and/or other ingredients.

The NSAIDs may include oxicams, propionic acids or acetic acids generally, and flurbiprofen, nabumetone, and/or other specific NSAIDs. The anticonvulsants may include topiramate and/or lamotrigine. The muscle relaxants may include baclofen, cyclobenzaprine, and/or other relaxants. The NMDA receptor antagonists may include ketamine. The opiate or opioid agonists may include C2 or C3 opiate agonists, or tramadol. The antidepressants may include amitriptyline, and/or other antidepressants.

The anticonvulsants, muscle relaxants, antidepressants, opiate or opioid agonists, and/or NMDA receptor antagonists may each be added to the silicone-based gel in a low concentration, such as between approximately 0.01% and approximately 5.0% by weight of the final silicone-based gel. The NSAIDs may be added to the silicone-based gel in an amount of between approximately 0.05% and approximately 25.0% by weight of the transdermal cream. Other amounts may be used, including those discussed elsewhere herein.

In one embodiment, the silicone-based gel may include cyclopentasiloxane; polysilicone-11; dimethicone; C30-45 alkyl cetearyl dimethicone crosspolymer; and/or other ingredients. The silicone-based gel may include a glucocorticoid (such as fluticasone) and/or an antihistamine (such as loratadine), both in an amount of between approximately 0.1% and approximately 5.0% by weight of the silicone-based gel. The silicone-based gel may also include a nerve depressant, such as gabapentin, in an amount of between approximately 5.0% and approximately 25.0% by weight of the silicone-based gel, and lidocaine and prilocaine, both in an amount of between approximately 1.0% and approximately 7.0% by weight of the silicone-based gel. The silicone-based gel may include other active ingredients, such as anticonvulsants, muscle relaxants, antidepressants, and/or opiate or opioid agonists in low concentrations, such as between approximately 0.01% and approximately 5.0% by weight of the final silicone-based gel. The silicone-based gel may also include NMDA receptor antagonists, NSAIDs, and/or other active ingredients.

The present invention may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims.

What is claimed is:

1. A silicone-based gel for topical application to skin, the silicone-based gel comprising:
   a silicone or silicone variant comprising C30-45 alkyl cetearyl dimethicone crosspolymer;
   fluticasone in an amount between approximately 0.1% and approximately 5.0% by weight of the silicone-based gel;
   an antihistamine in an amount between approximately 0.1% and approximately 5.0% by weight of the silicone-based gel, the antihistamine comprising one or more of loratadine, azelastine, or levocetirizine;
   a gabapentin in an amount between approximately 1.0% and approximately 25.0% by weight of the silicone-based gel; and
   lidocaine and prilocaine, each in an amount between approximately 1.0% and approximately 7.0% by weight of the silicone-based gel.

2. The silicone-based gel of claim 1, wherein the silicone-based gel further comprises at least approximately 50% silicone or silicone variant.

3. The silicone-based gel of claim 2, wherein the silicone or silicone variant further comprises cyclopentasiloxane, polysilicone-11, and dimethicone.

4. The silicone-based gel of claim 3, wherein the silicone or silicone variant further comprises tocopheryl acetate and BHT (butylated hydroxytoluene).

5. The silicone-based gel of claim 4, wherein the silicone-based gel is devoid of at least one of a NSAID (Non-Steroidal Anti-Inflammatory Drug) or a NMDA (N-methyl-D-aspartate) receptor antagonist.

6. The silicone-based gel of claim 4, further comprising a NSAID (Non-Steroidal Anti-Inflammatory Drug) or an anticonvulsant in an amount of between approximately 0.05% and approximately 5.0% by weight of the silicone-based gel.

7. The silicone-based gel of claim 1, wherein the silicone or silicone variant further comprises cyclopentasiloxane, polysilicone-11, and/or dimethicone.

8. The silicone-based gel of claim 7, wherein the silicone-based gel is devoid of at least one of a NSAID (Non-Steroidal Anti-Inflammatory Drug) or a NMDA (N-methyl-D-aspartate) receptor antagonist.

9. The silicone-based gel of claim 7, further comprising a NSAID (Non-Steroidal Anti-Inflammatory Drug) or an anticonvulsant in an amount of between approximately 0.05% and approximately 5.0% by weight of the silicone-based gel.

10. The silicone-based gel of claim 1, wherein the silicone or silicone variant further comprises tocopheryl acetate and BHT (butylated hydroxytoluene).

11. The silicone-based gel of claim 1, wherein the silicone-based gel is devoid of at least one of a NSAID (Non-Steroidal Anti-Inflammatory Drug) or a NMDA (N-methyl-D-aspartate) receptor antagonist.

12. The silicone-based gel of claim 1, further comprising a NSAID (Non-Steroidal Anti-Inflammatory Drug) or an anticonvulsant in an amount of between approximately 0.05% and approximately 5.0% by weight of the silicone-based gel.

13. The silicone-based gel of claim 1, wherein the gabapentin is present in an amount between approximately 10.0% and approximately 20.0% by weight of the silicone-based gel.

14. The silicone-based gel of claim 1, wherein the antihistamine is present in an amount between approximately 2.0% and approximately 4.0% by weight of the silicone-based gel.

* * * * *